(12) United States Patent
Bonnekessel et al.

(10) Patent No.: US 9,598,428 B2
(45) Date of Patent: Mar. 21, 2017

(54) METHOD FOR PREPARING A PYRIPYROPENE COMPOUND

(71) Applicant: BASF SE, Ludwigshafen (DE)

(72) Inventors: Melanie Bonnekessel, Ludwigshafen (DE); Wolfgang Reichert, Frankenthal (DE); Ralf Hoock, Ludwigshafen (DE); Thomas Kaeding, Mannheim (DE); Christopher Koradin, Gommersheim (DE); Andreas Pletsch, Limburgerhof (DE); Manfred Ehresmann, Maxdorf (DE); Hartwig Schroeder, Nussloch (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/760,302

(22) PCT Filed: Jan. 15, 2014

(86) PCT No.: PCT/EP2014/050654
§ 371 (c)(1),
(2) Date: Jul. 10, 2015

(87) PCT Pub. No.: WO2014/111398
PCT Pub. Date: Jul. 24, 2014

(65) Prior Publication Data
US 2016/0046644 A1    Feb. 18, 2016

Related U.S. Application Data

(60) Provisional application No. 61/753,023, filed on Jan. 16, 2013.

(30) Foreign Application Priority Data

Jan. 16, 2013   (EP) .................. 13151492

(51) Int. Cl.
A01N 43/90    (2006.01)
A01N 53/00    (2006.01)
C07D 493/04   (2006.01)

(52) U.S. Cl.
CPC ........ C07D 493/04 (2013.01); A01N 43/90 (2013.01); A01N 53/00 (2013.01)

(58) Field of Classification Search
CPC ....... C07D 493/04; A01N 53/00; A01N 43/90
USPC .................................... 546/283.1
See application file for complete search history.

(56) References Cited

FOREIGN PATENT DOCUMENTS

| EP | 1889540 | 2/2008 |
|---|---|---|
| EP | 2107060 | 10/2009 |
| EP | 2119361 | 11/2009 |
| EP | 2186815 | 5/2010 |
| EP | 2223599 | 9/2010 |
| EP | 2426124 | 3/2012 |
| WO | WO 2008013336 | 1/2008 |
| WO | WO 2011108155 | 9/2011 |

OTHER PUBLICATIONS

International Preliminary Report on Patentability, issued in PCT/EP2014/050654, dated Jul. 21, 2015.
International Search Report, issued in PCT/EP2014/050654, dated Mar. 25, 2014.

*Primary Examiner* — Noble Jarrell
*Assistant Examiner* — Daniel Carcanague
(74) *Attorney, Agent, or Firm* — Brinks Gilson & Lione

(57) ABSTRACT

The present invention relates to a method for preparing the pyripyropene compound of the formula (I) which method comprises the following steps: i) subjecting a pyripyropene compound of formula Pyripyropene A to an alkaline hydrolysis to yield a 1,7,11 -trideacetylpyripyropene A, ii) reacting 1,7,11-trideacetylpyripyropene A obtained in step i) with cyclopropane carbonyl chloride to yield a raw product containing the pyripyropene compound of formula (I); iii) subjecting the raw product of step ii) to crystallization to yield a crystalline pyripyropene compound of formula (I) and a mother liquor; and iv) recycling the mother liquor or a pyripyropene compound containing fraction thereof to the alkaline hydrolysis of step i).

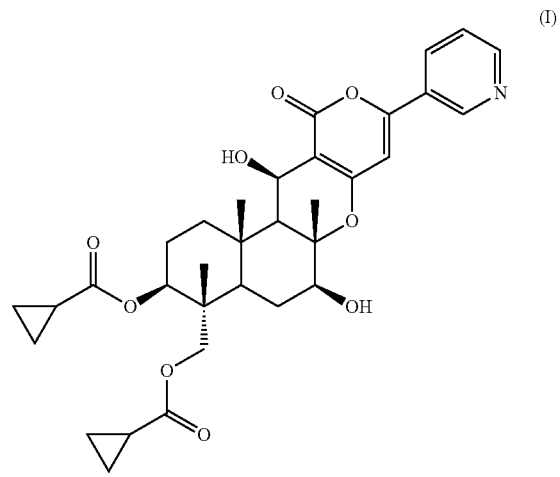

15 Claims, No Drawings

METHOD FOR PREPARING A PYRIPYROPENE COMPOUND

This application is a National Stage application of International Application No. PCT/EP2014/050654, filed Jan. 15, 2014, which claims the benefit of U.S. Provisional Application No. 61/753,023, filed Jan. 16, 2013. This application also claims priority under 35 U.S.C. §119 to European Patent Application No. 13151492.9, filed Jan. 16, 2013.

The present invention relates to a method for preparing the pyripyropene compound of the formula I Formula I

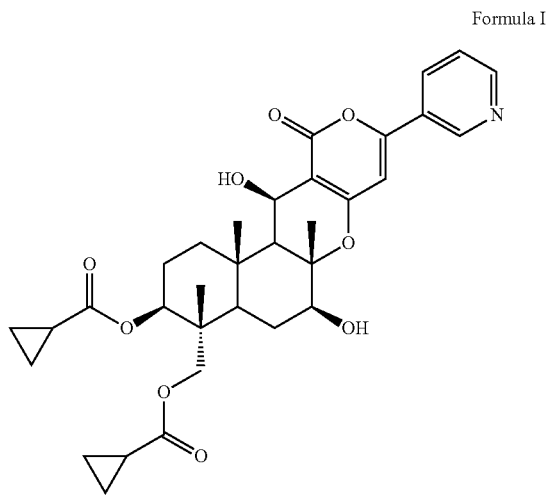

The pyripyropene compound of formula I, also termed 1,11-di-O-cyclopropanecarbonyl-1,7,11-triedeacetylpyripyropene A, is a new pesticide compound having promising insecticidal activities (see e.g. EP 1889540, EP 2119361 and EP 2223599).

The synthesis of the pyripyropene compound of formula I, as described in EP 1889540, includes the hydrolysis of a 1,7,11-tri-O-acetyl compound of the formula II to obtain the 1,7,11-trideacyl compound of the formula III, followed by reaction of the compound of formula III with cyclopropane carboxylic acid to afford 1,7,11-tri-O-cyclopropyl carbonyl compound of the formula IVa (=compound of the formula IV, where $R^a$=H, $R^b$=$R^c$=$R^d$=cyclopropylcarbonyl), which is subsequently subjected to a partial hydrolysis to afford the compound of the formula I together with other by-products.

Formula II

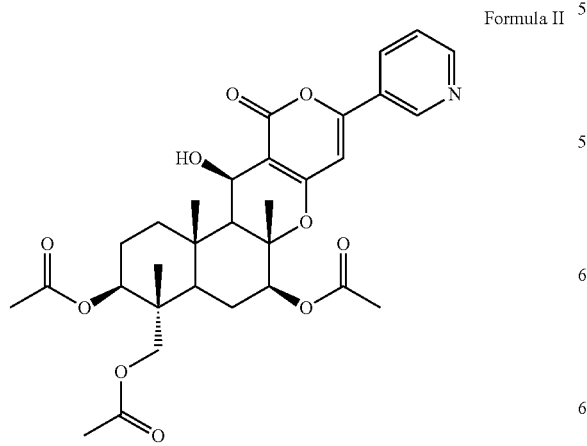

Formula III

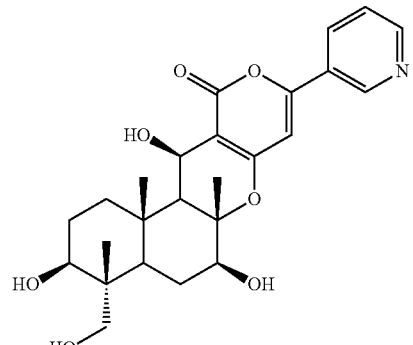

Formula IV

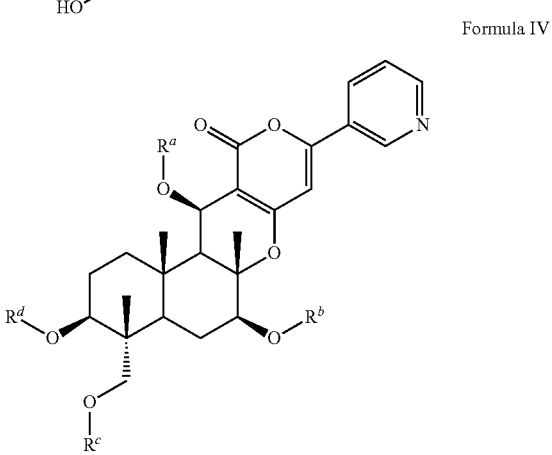

EP 2186815 discloses a process for preparing the compound of formula I, which comprises hydrolyzing the acetyl moiety at the 7-position of the compound of formula II with a base, protecting the thus formed hydroxyl group at the 7-position, then hydrolyzing the acetyl groups at the 1- and 11-position, acylating the 1- and 11-position with cyclopropane carbonyl chloride, and then removing the protective group. Due to the large number of reaction steps, the process is tedious and the deacetylation at the 7-position has to performed carefully to achieve the required selectivity.

EP 2426124 discloses a process for preparing the compound of formula I, which comprises direct acylation of the compound of formula III at the 1-position and the 11-position. Although, the four hydroxyl groups in the compound of formula III show significantly different reactivity, the acylation is not very selective with regard to the compound of formula I and both incomplete acylation, acylation of the wrong OH groups and side reactions such as elimination of water may occur. Moreover, the starting compound of formula III may also contain impurities that may react in the acylation reaction. Therefore, the obtained raw product contains significant amounts of by-products from which the compound of formula I has to be separated. Thus, it is necessary to purify the obtained acylation product by chromatography or crystallization resulting in a considerable loss of product and the obtained yields are low, i.e. below 45%. Moreover, the obtained purities are only moderate and further crystallization is required resulting in further loss of valuable products.

It is therefore an object of the present invention to provide a process for the preparation of the compound of formula I, which provides the compound of formula I with good yields and also high purity. Moreover, the process should allow for reducing the reaction time and it should be workable on industrial scale.

It was surprisingly found that these and further objectives are solved by the process as described hereinafter. In particular, it was found that the mother liquor of a crystallization of the raw-product obtained from the acylation reaction of the compound of formula III with cyclopropane carbonyl chloride contains significant amounts of pyripyropene compounds, which can be saponified to the compound of formula III. Thus, the fraction of pyripyropene compounds contained in the mother liquor can be used as a further starting material in addition to the compound of formula II for the production of the compound of formula I by recycling this fraction of pyripyropene compounds to the saponification of the compound of formula II and using the thus obtained mixture in the subsequent acylation reaction with cyclopropane carbonyl chloride. Surprisingly, the recycling of the fraction of pyripyropene compounds contained in the mother liquor is not detrimental with regard to purity and yields of the obtained pyripyropene compound of formula I. Rather, the recycling allows for higher concentrations and shorter reaction times in the acylation reaction of the compound of formula III. Moreover, the recycling reduces yield losses as by-products from the acylation reaction are recovered.

Thus, the present invention relates to a method for preparing pyripyropene compound of the formula I, which method comprises the following steps:

i) subjecting a pyripyropene compound of formula II (pyripyropene A) to an alkaline hydrolysis to yield a pyripyropene compound of the formula III, ii) reacting the pyripyropene compound of formula III obtained in step i) with cyclopropane carbonyl chloride to yield a raw product containing the pyripyropene compound of formula I;

iii) subjecting the raw product of step ii) to crystallization to yield a crystalline pyripyropene compound of formula I and a mother liquor; and iv) recycling the mother liquor or a pyripyropene compound containing fraction thereof to the alkaline hydrolysis of step i).

The process of the invention starts from the 1,7,11-tri-O-acetyl compound of the formula II, which is a naturally occurring substance, namely pyripyropene A, and which can be prepared by analogy to the methods described in WO 94/09147, EP 1889540, WO 2004/060065, EP 2186815 and the prior art cited therein.

In step i) the 1,7,11-tri-O-acetyl compound of the formula II is saponified/hydrolyzed to obtain the 1,7,11-trideacyl compound of the formula III. According to the present invention, the mother liquor of a previous run or a pyripyropene compound containing fraction thereof is recycled into the saponification reaction of said step i) to obtain further amounts of the 1,7,11-trideacyl compound of the formula III by saponification/hydrolysis of the pyripyropene compounds contained in the mother liquor.

Recycling of the mother liquor or a pyripyropene compound containing fraction thereof into the saponification of step i) may be achieved by combining the mother liquor or a pyripyropene compound containing fraction thereof with fresh compound of the formula II and subjecting the thus obtained mixture to saponification conditions. Recycling of the mother liquor or of a pyripyropene compound containing fraction thereof is preferably achieved by first subjecting the pyripyropene compounds contained in the mother liquor to a saponification/hydrolysis reaction to achieve an at least partial hydrolysis of the ester groups present in the pyripyropene compounds contained in the mother liquor, adding to the thus obtained mixture fresh compound of formula II and continuing the saponification/hydrolysis to yield the compound of formula III. It is of course also possible to first subject fresh compound of formula II to a saponification/hydrolysis reaction to achieve an at least partial hydrolysis of the ester groups present therein, adding to the thus obtained mixture the pyripyropene compounds contained in the mother liquor and continuing the saponification/hydrolysis to yield the compound of formula III.

In particular the relative amounts of the fresh pyripyropene compound of formula II and mother liquor or pyripyropene compound containing fraction recycled into the alkaline hydrolysis of step i) is chosen such that molar ratio of the recycled pyripyropene compounds, contained in the mother liquor or in the fraction thereof, and fresh pyripyropene of formula II is in the range from 1:5 to 5:1 and in particular from 1:3 to 3:1.

The pyripyropene compounds contained in the mother liquor usually comprise at least one compound of the formula IV, where at least one, in particular 1, 2 or 3 of the radicals $R^a$, $R^b$, $R^c$ and $R^d$ is cyclopropylcarbonyl, while the others of $R^a$, $R^b$, $R^c$ and $R^d$ are hydrogen. In particular, the pyripyropene compound contained in the mother liquor comprises two or more compounds of the formula IV, selected from a) the 1,7,11-tri-O-cyclopropylcarbonyl compound of the formula IVa, i.e. of the formula IV, where $R^a$=H and where $R^b$=$R^c$=$R^d$=cyclopropylcarbonyl;

b) the 1-, 7- and 11-mono-O-cyclopropylcarbonyl compounds of the formula IVb, i.e. of the formula IV, where $R^a$=H and where one of $R^b$, $R^c$ and $R^d$ is cyclopropylcarbonyl, while the other two of of $R^b$, $R^c$ and $R^d$ are hydrogen;

c) the 1,7-, 1,11- and 7,11-di-O-cyclopropylcarbonyl compounds of the formula IVc, i.e. of the formula IV, where $R^a$=H and where two of $R^b$, $R^c$ and $R^d$ are cyclopropylcarbonyl, while the others are one of $R^b$, $R^c$ and $R^d$ is hydrogen.

The pyripyropene compounds contained in the mother liquor frequently comprise at least the compound of formula II and at least one further compound of the formula IV, where at least one, in particular 1, 2 or 3 of the radicals $R^a$, $R^b$, $R^c$ and $R^d$ is cyclopropylcarbonyl, while the others of $R^a$, $R^b$, $R^c$ and $R^d$ are hydrogen. The pyripyropene compounds contained in the mother liquor usually comprise at least the compound of formula II and at least one further compound of the formula IV, selected from the compounds IVa, IVb and IVc.

The saponification or hydrolysis of the 1,7,11-tri-O-acetyl compound of the formula II and the fraction of pyripyropene compounds contained in the mother liquor can be achieved according to standard methods as described e.g. in EP 1889540.

The saponification in step i) is usually achieved by reacting the compound of formula II or the fraction of pyripyropene compounds contained in the recycled mother liquor or the mixture thereof with a base selected from alkali metal hydroxide, earth alkaline metal hydroxides, alkali metal $C_1$-$C_4$-alkoxides and earth alkaline metal $C_1$-$C_4$-alkoxides. Preferred bases are alkalimetal hydroxides and alkalimetal methoxides, in particular sodium hydroxide and sodium methoxide. The amount of base is generally from 0.2 to 2 equivalents, in particular from 0.2 to 1.5 equivalents, based on the total amount of ester groups present in the compound of formula II and the pyripyropene compounds recycled into the step i). Preferably, the amount of base is chosen such that the pH-value of the resulting reaction mixture at 20 to 50° C., e.g. at 20° C., does not exceed pH 13 and in particular is in the range of pH 10 to pH 13.

The saponification reaction may be performed in water, in an organic solvent or in a mixture of an organic solvent with water. Preferably, the saponification is performed in an organic solvent or in a mixture of an organic solvent with water. In particular, the solvent used for saponification comprises at least 90% by weight, based on the total amount of solvent, of an organic solvent.

The concentration of pyripyropene compounds during saponification is generally from 1 to 50% by weight, in particular from 5 to 40% by weight, based on the total weight of the reaction mixture.

Suitable organic solvents for saponification are any organic solvents, which are inert under the reaction conditions. Suitable organic solvents for saponification include $C_1$-$C_4$-alkanols such as methanol, ethanol, isopropanol, n-butanol, aliphatic or alicyclic ethers such as diethyl ether, di-n-propyl ether, diisopropyl ether, methyl tert.-butyl ether, ethyl tert.-butyl ether, tetrahydrofurane, methyltetrahydrofurane and dioxane, aromatic hydrocarbons such as toluene or ethyl benzene and mixtures thereof. Preferably, the organic solvent for saponification comprises at least one $C_1$-$C_4$-alkanol, especially methanol. In particular, the organic solvents for saponification comprises at least one $C_1$-$C_4$-alkanol, especially methanol, and at least one aromatic hydrocarbon, especially toluene and/or ethyl benzene. More preferably, the organic solvents for saponification is a mixture of at least one $C_1$-$C_4$-alkanol, especially methanol, and at least one aromatic hydrocarbon, especially toluene and/or ethyl benzene. Especially, the saponification is performed in solvent, comprising at least 90%, based on the total amount of solvent, of a mixture of at least one $C_1$-$C_4$-alkanol, especially methanol, and at least one aromatic hydrocarbon, especially toluene and/or ethyl benzene. In another special embodiment, the saponification is performed in mixture of water and an organic solvent, which is a mixture of at least one $C_1$-$C_4$-alkanol, especially methanol, and at least one aromatic hydrocarbon, especially toluene and/or ethyl benzene. In a further special embodiment, the saponification is performed in mixture of water and at least one $C_1$-$C_4$-alkanol, especially methanol.

The saponification of step i) is generally performed at a temperature in the range from 10 to 100° C., in particular from 15 to 60° C., especially from 20 to 50° C.

In step ii) of the process of the present invention the pyripyropene compound of formula III, which is obtained in step i), is reacted with cyclopropane carbonyl chloride to yield a raw product containing the pyripyropene compound of formula I.

The reaction of step ii) is usually performed in a solution or suspension of the compound of formula III in a polar aprotic solvent. Suitable polar aprotic solvents are in particular polar aprotic amides, e.g. N—$C_1$-$C_3$-alkyl lactams such as N-methyl pyrrolidone or N-ethyl pyrrolidone, N,N-di-$C_1$-$C_3$-alkyl amides of $C_1$-$C_4$ alkanoic acids such as N,N-dimethyl formamide or N,N-dimethyl acetamide, N,N'-di-$C_1$-$C_3$-alkyl imidazolin-2-ones such as N,N-dimethyl imidazolin-2-on, and N,N,N',N'-tetra-$C_1$-$C_3$-alkyl ureas such as N,N,N',N'-tetramethyl urea and mixtures thereof. In particular, the polar aprotic solvents is selected from N-methyl pyrrolidone and N,N-dimethyl acetamide. Especially, the polar aprotic solvent is N,N-dimethyl acetamide.

Frequently, the relative amounts of the compound of formula III and the polar aprotic solvent, are chosen such that the weight ratio of polar aprotic solvent to compound III is from 6:1 to 1:1 and in particular from 4:1 to 2:1 and especially from 3:1 to 2.2:1.

Frequently, the amount of cyclopropyl carbonyl chloride in step ii) is from 2 mol to 5 mol, in particular from 2.5 to 4 mol, especially from 2.8 to 3.2 mol, per mol of the compound of formula III. Preferably, the cyclopropyl carbonyl chloride is added to a solution or suspension of the compound of the formula I in the aprotic polar solvent. Preferably, the addition is performed in a controlled manner such that the temperature in the reaction vessel does not exceed 15° C., in particular 10° C.

The reaction of step ii) is generally performed at a temperature in the range from −15 to +15° C., in particular from −10 to +10° C., especially from −5 to +5° C. The reaction time is generally from 10 to 80 h, in particular form 15 to 48 h, especially form 20 to 45 h.

The reaction of step ii) is preferably stopped (i.e. quenched) by addition of water or by addition of an aqueous base. Suitable bases include in particular inorganic bases, e.g. alkalimetal hydrogen carbonates, such as sodium or potassium hydrogen carbonate, alkalimetal carbonates, such as sodium or potassium carbonate, and alkalimetal hydroxides, such as sodium or potassium hydroxide. Preferred bases are alkalimetal hydrogen carbonates and alkalimetal carbonates, in particular sodium hydrogen carbonate and sodium carbonate, especially sodium carbonate. The amount of base is generally chosen such that the resulting pH of the reaction mixture is in the range form pH 1 to pH 8, in particular form pH 2 to pH 7.

Generally, the thus obtained, optionally quenched reaction mixture of step ii) is subjected to an aqueous work-up. For the aqueous work-up, the optionally quenched reaction mixture of step ii) is usually partitioned between an organic solvent of limited solubility in water and an aqueous phase. The aqueous phase serves as an extractant for polar by-products of the reaction mixtures such as salts and the polar aprotic solvent. Suitable organic solvents for aqueous work-up include generally those having a solubility in water of not more than 100 g/l at 20° C., in particular $C_1$-$C_4$-alkyl esters of $C_1$-$C_4$-alkanoic acids, especially $C_1$-$C_4$-alkyl esters of acetic acid or propionic acid, such as ethyl acetate, butyl acetate, or ethyl propionate, and $C_1$-$C_4$-alkyl benzenes such as toluene and ethyl benzene, as well as mixtures thereof.

Preferably, the aqueous work up comprises an aqueous extraction of the optionally quenched reaction mixture of step ii) with an acidic aqueous extractant. Suitable aqueous extractants are aqueous solutions of organic or inorganic acids, such as phosphoric acid, sulfuric acid, hydrochloric acid, formic acid or acetic acid. Preferred acidic aqueous extractants contain phosphoric acid. Particularly preferred acidic extractants are aqueous solutions of phosphoric acid. Preferably, the concentration of the acid in the acidic aqueous extractant is from 0.01 to 1 mol/l, in particular from 0.02 to 0.5 mol/l.

The acidic extraction is usually performed as follows: The optionally quenched reaction mixture is diluted with an organic solvent of limited solubility in water, generally those having a solubility in water of not more than 100 g/l at 20° C., in particular $C_1$-$C_4$-alkyl esters of $C_1$-$C_4$-alkanoic acids, especially $C_1$-$C_4$-alkyl esters of acetic acid or propionic acid, such as ethyl acetate, butyl acetate, or ethyl propionate, and $C_1$-$C_4$-alkyl benzenes such as toluene and ethyl benzene, as well as mixtures thereof. The thus obtained dilution is then extracted with the acidic extractant. The acidic extraction may be followed by extraction of the organic dilution with water and/or extraction with an aqueous solution of a base, such as an aqueous solution of alkalimetal carbonate or alkalimetal hydrogen carbonate. The aqueous phase, optionally after neutralization to pH>6, in particular to a pH in the range of pH 6.5 to pH 9, may be re-extracted with an organic solvent or solvent mixture having a solubility in water of not more than 100 g/l at 20° C. as described above. The re-extracted organic phase may be combined with the mother liquor of the subsequent crystallization.

The acidic extraction and optionally further extractions are generally performed at a temperature between the freezing point and the boiling point of the solvent/water mixture. Frequently, the acidic extraction and optionally further extractions are generally performed at a temperature in the range form 5 to 90° C., in particular form 10 to 70° C. and especially from 15 to 55° C.

According to the invention, the compound of formula I is obtained by subjecting the raw product of step ii) to a crystallization in order to yield pyripyropene compound of formula I in crystalline form. Additionally, a mother liquor is obtained which contains the aforementioned pyripyropene compounds of formula IV and optionally unreacted compound of formula III.

The crystallization of the raw product may comprise a single crystallization step or two or more crystallization steps.

The crystallization of the raw product may usually be effected from a solution of the raw product in a suitable organic solvent. Suitable organic solvents for crystallization include e.g. $C_1$-$C_4$-alkyl esters of $C_1$-$C_4$-alkanoic acids, especially $C_1$-$C_4$-alkyl esters of acetic acid or propionic acid, such as ethyl acetate, butyl acetate, or ethyl propionate, and $C_1$-$C_4$-alkyl benzenes such as toluene and ethyl benzene, as well as mixtures thereof and mixtures thereof with one or more co-solvents such as $C_5$-$C_{10}$-aliphatic or $C_5$-$C_{10}$-cycloaliphatic hydrocarbons, e.g. hexanes, heptanes, cyclohexane, methylcyclohexane etc. Preferably, the solvent comprises at least 45% by weight, in particular at least 55% by weight, e.g. 45 to 80% by weight, in particular 55 to 80% by weight, based on the total amount of solvent, of at least one aprotic solvent selected from aromatic hydrocarbon solvent, $C_1$-$C_4$-alkyl acetates and mixtures thereof. Particular preferred solvents for crystallization are selected from ethyl acetate, toluene, ethylbenzene and mixtures thereof and mixtures thereof with one or more co-solvents such as cyclohexane. Especially, the solvent comprises at least 45% by weight, in particular at least 55% by weight, e.g. 45 to 80% by weight, in particular 55 to 80% by weight, based on the total amount of solvent, of a solvent selected from ethyl acetate, toluene, ethylbenzene and mixtures thereof. The solution of the raw product may be the solution obtained after aqueous work-up of the reaction mixture of step ii). The solution of the raw product may be obtained by dissolving a concentrated or dried raw product of the aqueous work-up in a suitable organic solvent as described above.

The concentration of the raw product in the solution prior to crystallization is generally from 10 to 40% by weight, in particular form 12 to 35% by weight, especially from 15 to 30% by weight, based on the total amount of solvent and raw product.

Crystallization of the compound of formula I is generally achieved by cooling a solution of the raw product or by concentrating a solution of the raw product or by combined measures. Preferably, the crystallization is effected from the solution having a first temperature by cooling the solution to a second temperature which is at least 10 K, in particular at least 20 K, e.g. from 10 to 80 K, in particular from 20 to 60 K, below the first temperature. The first temperature is preferably in the range form 40 to 90° C., in particular form 45 to 80° C., especially from 50 to 70° C., while the second temperature is preferably in the range from −15 to 50° C., in particular from 0 to 40° C., especially from 5 to 35° C. Preferably, the cooling rate does not exceed 20 K/h and is in particular in the range from 1 to 20 K/h, especially from 2 to 15 K/h.

Crystallization may be promoted by adding seed crystals of the compound of formula I to the solution for crystallization. Preferably, seed crystals are added at a temperature in the range from 30 to 70° C., especially in the range from 40 to 60° C. The amount of seed crystals added is generally from 0.1 to 10% by weight, in particular from 0.2 to 5% by weight, based on the amount of solid raw product contained in the solution for crystallization.

The obtained crystalline compound of the formula I is then separated from its mother liquor. Separation can be achieved by suitable techniques for separating liquids from solids, e.g. by filtration or centrifugation.

The thus obtained crystalline material may be washed with a suitable organic solvent in order to remove residues of the mother liquor adhering to the crystalline material. The solvent used for washing may be combined with the mother liquor of the crystallization, as it contains a certain amount of the compound of formula I. Suitable solvents for washing include the solvents mentioned as suitable solvents for crystallization. Preferably, the solvent for washing comprises at least 50% by weight, in particular at least 80% by weight, based on the total amount of solvent, of at least one aprotic solvent selected from aromatic hydrocarbon solvent, $C_1$-$C_4$-alkyl acetates and mixtures thereof. Particular preferred solvents for washing are selected from ethyl acetate, toluene, ethylbenzene and mixtures thereof and mixtures thereof with one or more co-solvents such as cyclohexane. Especially, the solvent for washing comprises at least 50% by weight, in particular at least 80% by weight, based on the total amount of solvent, of a solvent selected from ethyl acetate, toluene, ethylbenzene and mixtures thereof. Preferably, washing is performed at a temperature of not more than 40° C., in particular not more than 30° C., e.g. at a temperature in the range from −15 to 40° C. in particular from 0 to 30° C.

The crystallization can be repeated one or more times, in particular once or twice, i.e. the obtained crystalline material can be crystallized again, in order to further increase the purity of the compound of formula I. The recrystallization can be performed in the same way as described for the crystallization of the raw product. The thereby obtained mother liquors and washings are preferably combined with the mother liquor and the washings obtained in the crystallization of the raw product and together recycled back into step i) of the inventive process.

By the process of the present invention, the compound of formula I is obtained in high yields and high purities of generally >90%, in particular >95%.

The following examples further illustrate the present invention.

EXPERIMENTS

The following abbreviations and terms are used in the following examples:
DMAC: N,N-dimethyl acetamide
MeOH Methanol
% b.w.: % by weight
v/v volume per volume Reference Example 1

250 g of the compound of formula III (purity 95%, 0.52 mol) were suspended in 625 g DMAC (purity 100%, 7.17 mol) and the solution was cooled to -3° C. 166 g cyclopropane carbonyl chloride (purity 98%, 1.56 mol) were added in 20 min, keeping the temperature below 0° C. The reaction was stirred for 33 h at 0° C. and then the reaction mixture was added to a mixture of 962 g sodium carbonate (10% b.w. in water, 0.91 mol) and 2110 g toluene (22.91 mol) at 20° C. (pH 7). The vessel was purged with 50 g of a 1:1-mixture (v/v) of DMAC : toluene. After phase separation at 23° C., the organic phase was successively washed twice with aqueous phosphoric acid (0.2 M, 750 mL, pH 2.3-2), once with aqueous phosphoric acid (0.035 M, 760 mL, pH 2.2), once with aqueous sodium carbonate (1% by weight, 745 mL, pH 7.3) and once with water (250 mL). Concentration of the organic phase in vacuo (70° C., 100 mbar) yielded 666 g of a 25.2% b.w. solution of the compound of formula I (0.28 mol, 54% yield), which can be subjected to crystallization.

Reference Example 2

250 g of the compound of formula III (purity 95%, 0.52 mol) were suspended in 625 g DMAC (purity 100%, 7.17 mol) and the solution was cooled to -3° C. 166 g cyclopropane carbonyl chloride (purity 98%, 1.56 mol) were added in 20 min, keeping the temperature below 0° C. The reaction was stirred for 32 h at 0° C. and then the reaction mixture was added to a mixture of 957 g sodium carbonate (10% in water, 0.91 mol) and 2110 g toluene (100%, 22.91 mol) at 20° C. (pH 6.3). The vessel was purged with 50 g of a 1:1-mixture (v/v) of DMAC : toluene. After phase separation at 23° C., the organic phase was successively washed twice with aqueous phosphoric acid (0.2 M, 750 mL, pH 2.1-1.8), once with aqueous phosphoric acid (0.035 M, 760 mL, pH 2.7), once with aqueous sodium carbonate (1% b.w., 745 mL, pH 7.2) and once with water (250 mL). Concentration of the organic phase in vacuo (70° C., 100 mbar) gave 666 g of a 25% b.w. solution of the compound of formula I. 630 g of said solution were heated to 55° C., seeded with 0.80 g of the compound of formula I and cooled down to 0° C. with 5 K/h and stirred for further 12 h. The obtained solid (162 g, toluene-wet) was filtered and washed with toluene (360 mL) at 0° C., yielding 726 g mother liquor 1. 159 g of the toluene-wet solid were suspended in 356 mL ethyl acetate, heated for 2 h to 70° C. to obtain a suspension which was afterwards cooled down to 20° C. with 10 K/h. Thereby the compound of formula I crystallized. The crystals were filtered off, washed with ethyl acetate (341 g mother liquor 2) and dried in vacuo, thereby yielding 126 g of the compound of formula I (purity 98%, 0.21 mol, yield 40%).

Example 1 (First Run)

250 g of the compound of formula III (purity 95%, 0.52 mol) were suspended in 625 g DMAC (purity 100%, 7.17 mol) and the solution was cooled to -3° C. 166 g cyclopropane carbonyl chloride (purity 98%, 1.56 mol) were added within 20 min, keeping the temperature below 0° C. The reaction was stirred for 43 h at 0° C. and then the reaction mixture was added to a mixture of 962 g sodium carbonate (10% b.w. in water, 0.91 mol) and 2110 g toluene (22.91 mol) at 15° C. (pH 7.1). The vessel was purged with 50 g of a 1:1-mixture (v/v) of DMAC: toluene. After phase separation at 15° C., the organic phase was successively washed twice with aqueous phosphoric acid (0.2 M, 750 mL, pH 2.1-2.0), once with aqueous phosphoric acid (0.035 M, 760 mL, pH 2.4), once with aqueous sodium carbonate (1% b.w., 745 mL, pH 7.3) and once with water (250 mL). Concentration of the organic phase in vacuo (70° C., 100 mbar) gave 666 g of a 25.4% b.w. solution of the compound of formula I. 640 g of said solution were heated to 55° C., seeded with 0.84 g of the compound of formula I and cooled down to 0° C. with 5 K/h and stirred for further 12 h. The obtained solid was filtered off, washed with toluene (280 mL and 80 mL), yielding 729 g mother liquor 1 and 187 g of the compound of formula I (toluene-wet). 175 g of the toluene-wet solid were suspended in 350 mL of ethyl acetate, heated for 2 h to 70° C. to obtain a suspension which was afterwards cooled down to 20° C. with 10 K/h. Thereby the compound of formula I crystallized. The crystals were filtered off, washed with 140 mL of ethyl acetate and dried in vacuo, thereby yielding 123 g of the compound of formula I (purity 98%, 0.21 mol, 40% yield) and 399 g of mother liquor 2. The combined aqueous phase and three acid phases (3951 g) were neutralized to pH 7.3 with 53 g of sodium carbonate (100%, 0.5 mol) and re-extracted three times with 400 g toluene at 70° C. yielding 1082 g of mother liquor 3.

Example 2

Recovery of the Compound of Formula III by Joint Saponification

The mother liquor 2 of Example 1 was evaporated at 60° C. and 100 mbar to dryness. Then mother liquors 1 and 3 of Example 1 were successively continuously evaporated until 358 g of a solution were obtained. The solution was diluted with MeOH (357 g) and 118 g of the resulting MeOH/toluene mixture containing 0.043 mol of the compound of formula I and derivatives IV were taken for the following saponification. 470 g MeOH was added to the mixture and the mixture was warmed to 30° C. 7.5 g sodium hydroxide (50%, 0.094 mol) were added and the reaction mixture stirred for 10 h (pH 12.9). Then 170 g of a solution of the compound of formula II in toluene (17.5% b.w., 0.051 mol) were added and stirring was continued for 4 h. After cooling to 22° C., the mixture was filtered and washed 2 times with MeOH (30 mL each) at 0° C. After drying at 100° C. in vacuo, 41.8 g of the compound of formula III (purity 91.8%, 0.084 mol, 89% yield) were obtained.

Example 3 (First Run)

60 g of the compound of formula III (purity 95%, 0.12 mol) were suspended in 150 g DMAC (purity 100%, 1.72 mol) and the solution was cooled to -3° C. 40 g cyclopropane carbonyl chloride (purity 98%, 0.37 mol) were added within 20 min, keeping the temperature below 0° C. The reaction mixture was stirred for 43 h at 0° C. and then added to a mixture of 232 g aqueous sodium carbonate (10% b.w. in water, 0.03 mol) and 850 g ethyl benzene (8.02 mol) at 15° C. (pH 7). The reaction vessel was purged with 15 g of DMAC. After phase separation at 70° C., the organic phase was successively washed three times with diluted aqueous phosphoric acid (0.1 M, 180 mL, pH 3.2-2.3) and once with water (180 mL, pH 2.8). Concentration of the organic phase in vacuo (70° C., 90 mbar) gave a 18% b.w. solution of the compound of formula I. The solution was heated to 55° C., seeded with the compound of formula I and cooled down to 0° C. with 5 K/h. The obtained solid was filtered off and washed with ethyl benzene (50 mL), yielding 205 g mother liquor 1 and 44 g of ethyl benzene-wet solid. 44 g of the ethyl benzene-wet solid were suspended in 88 mL ethyl acetate, heated to 70° C. for 2 h and afterwards cooled down to 20° C. with 10 K/h. Thereby the compound of formula I crystallized. The crystals were filtered off, washed with 50 mL ethyl acetate (82 g mother liquor 2) and dried in vacuo, thereby yielding 31.5 g of the compound of formula I (97% purity, 0.05 mol, 41% yield).

Example 4

Recovery of the Compound of Formula III by Joint Saponification 82 g of the mother liquor 2 of example 3 were evaporated to dryness at 80° C. (200→20 mbar). To the obtained residue 205 g of mother liquor 1 were added and the obtained mixture was concentrated to 80 g at 40 mbar and 65° C. The thus obtained solution was diluted with 720 g MeOH to yield a solution containing 55 mmol of the compound of formula I and derivatives. The solution was warmed to 30° C. and 5 g sodium hydroxide (50%, 62.5 mmol) were added (pH 12.2) and the resulting mixture was stirred for 24 h. Then 300 g a solution of the compound of formula II in ethyl benzene (22.4% b.w., 115 mmol) and 6 g of aqueous sodium hydroxide (50% b.w., 75.0 mmol) were successively added. After 3 h, the reaction mixture was cooled to 22° C. The precipitate was filtered off and washed twice with MeOH (60 mL each). Drying of the solids at 25 mbar and 100° C. yielded 73 g of the compound of formula III (94.4% purity, 151 mmol, 88% yield).

Example 5

Preparation of the Compound of Formula I by Using the Recovered Material of Example 4

60 g of the compound of formula III obtained in example 4 (purity 94.4%, 0.12 mol) were suspended in 150 g DMAC (purity 100%, 1.72 mol) and the suspension was cooled to −3° C. 40 g cyclopropane carbonyl chloride (purity 98%, 0.37 mol) were added within 20 min, keeping the temperature below 0° C. The reaction mixture was stirred for 41 h at 0° C. and then added to a mixture of 232 g sodium carbonate (10% b.w. in water, 0.03 mol) and 852 g ethyl benzene (100%, 8.02 mol) at 15° C. (pH 7). The vessel was purged with 15 g of DMAC. After phase separation at 70° C., the organic phase was successively washed three times with diluted aqueous phosphoric acid (0.1 M, 180 mL, pH 2.8-2.3) and once with water (180 mL, pH 2.9). Concentration of the organic phase in vacuo (70° C., 90 mbar) gave a 18% b.w. solution of the compound of formula I. The solution was heated to 55° C., seeded with the compound of formula I and cooled down to 0° C. with 5 K/h. The obtained solid was filtered off and washed with ethyl benzene (50 mL), yielding 211 g mother liquor 1 and 44 g of an ethyl benzene-wet solid. 44 g of the ethyl benzene-wet solid were suspended in 88 mL ethyl acetate, heated to 70° C. for 2 h and afterwards cooled down to 20° C. with 10 K/h. Thereby the compound of formula I crystallized. The crystals were filtered off, washed with 50 mL ethyl acetate (82 g mother liquor 2) and dried in vacuo, thereby yielding 29.5 g of the compound of formula I (98% purity, 0.05 mol, 41% yield).

We claim:
1. A method for preparing the pyripyropene compound of the formula I

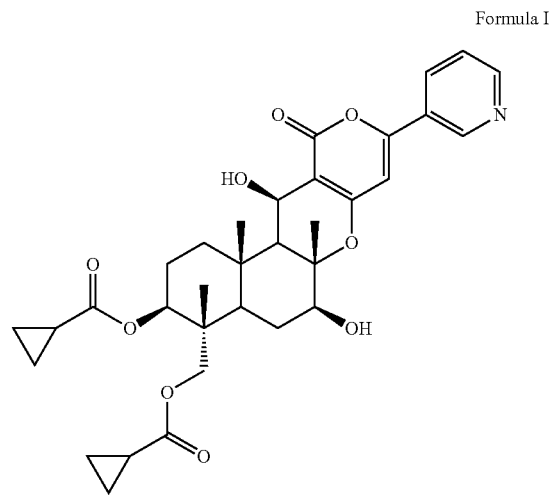

Formula I the method comprising the following steps:
i) subjecting a pyripyropene compound of formula II to an alkaline hydrolysis to yield a pyripyropene compound of the formula III, Formula II Formula III ii) reacting the pyripyropene compound of formula III obtained in step i) with cyclopropane carbonyl chloride to yield a raw product containing the pyripyropene compound of formula I;

iii) subjecting the raw product of step ii) to crystallization to yield a crystalline pyripyropene compound of formula I and a mother liquor; and iv) recycling the mother liquor or a pyripyropene compound containing fraction thereof to the alkaline hydrolysis of step i) by one of the following measures:

combining the mother liquor or pyripyropene compound containing fraction thereof with fresh compound of the formula II and subjecting the thus obtained mixture to the alkaline hydrolysis of step i);

subjecting the pyripyropene compounds contained in the mother liquor to an alkaline hydrolysis to achieve an at least partial hydrolysis of the ester groups present in the pyripyropene compounds contained in the mother liquor, adding to the thus obtained mixture fresh compound of formula II and continuing the alkaline hydrolysis; or subjecting fresh compound of formula II to an alkaline hydrolysis to achieve an at least partial hydrolysis of the ester groups present therein, adding to the thus obtained mixture the pyripyropene compounds contained in the mother liquor and continuing the alkaline hydrolysis.

2. The method of claim 1, wherein step ii) is performed in a solution or suspension of the compound of formula III in a polar aprotic solvent, which is selected from N-methyl pyrrolidone and dimethyl acetamide.

3. The method of claim 2, wherein the weight ratio of polar aprotic solvent to compound III is from 6:1 to 1:1.

4. The method of claim 1, wherein the reaction mixture of step ii) is subjected to an aqueous extraction with an acidic aqueous extractant.

5. The method of claim 1, wherein the reaction mixture of step ii) is subjected to a workup comprising a neutralization of the reaction mixture and a subsequent aqueous extraction with an acidic aqueous extractant.

6. The method of claim 4, wherein the acidic aqueous extractant contains phosphoric acid.

7. The method of claim 1, wherein the crystallization of the raw product is achieved from a solution of the raw product in at least one organic solvent, which solvent comprises at least 50%, based on the total amount of solvent, of at least one aprotic solvent selected from aromatic hydrocarbon solvent, $C_1$-$C_4$-alkyl acetates and mixtures thereof.

8. The method of claim 1, wherein the relative amount of the pyripyropene compound of formula II and mother liquor or pyripyropene compound containing fraction recycled into the alkaline hydrolysis of step i) is such that molar ratio of the recycled pyripyropene compound and fresh pyripyropene of formula II is in the range from 1:5 to 5:1.

9. The method of claim 1, wherein hydrolysis in step i) is achieved by reacting the compound of formula II with a base selected from the group consisting of alkali metal hydroxide, earth alkaline metal hydroxides, alkali metal $C_1$-$C_4$-alkoxides and earth alkaline metal $C_1$-$C_4$-alkoxides, in an organic solvent or in a mixture of an organic solvent with water.

10. The method of claim 9, wherein the organic solvent comprises at least one $C_1$-$C_4$-alkanol.

11. The method of claim 9, wherein the organic solvent comprises at least 90%, based on the total amount of organic solvent, of a mixture of at least one alkyl aromatic hydrocarbon solvent, and at least one $C_1$-$C_4$-alkanol.

12. The method of claim 8, wherein the relative amount of the pyripyropene compound of formula II and mother liquor or pyripyropene compound containing fraction recycled into the alkaline hydrolysis of step i) is such that molar ratio of the recycled pyripyropene compound and fresh pyripyropene of formula II is in the range from 1:3 to 3:1.

13. The method of claim 9, wherein the base is selected from the group consisting of sodium hydroxide and sodium methoxide.

14. The method of claim 10, wherein the organic solvent comprises methanol.

15. The method of claim 11, wherein the organic solvent comprises at least 90%, based on the total amount of organic solvent, of a mixture of toluene and/or ethyl benzene, and methanol.

* * * * *